US011861832B2

United States Patent
Warier et al.

(10) Patent No.: US 11,861,832 B2
(45) Date of Patent: Jan. 2, 2024

(54) AUTOMATICALLY DETERMINING A BROCK SCORE

(71) Applicant: Qure.ai Technologies Private Limited, Mumbai (IN)

(72) Inventors: Prashant Warier, Mumbai (IN); Ankit Modi, Koderma (IN); Preetham Putha, Guntur (IN); Prakash Vanapalli, Vishakapatnam (IN); Vikash Challa, Vizianagaram (IN); Ranjana Devi, Hyderabad (IN); Ritvik Jain, Gaya (IN)

(73) Assignee: QURE.AI TECHNOLOGIES PRIVATE LIMITED, Mumbai (IN)

( * ) Notice: Subject to any disclaimer, the term of this patent is extended or adjusted under 35 U.S.C. 154(b) by 0 days.

(21) Appl. No.: 18/073,697

(22) Filed: Dec. 2, 2022

(65) Prior Publication Data

US 2023/0177687 A1 Jun. 8, 2023

Related U.S. Application Data

(63) Continuation-in-part of application No. 17/457,465, filed on Dec. 3, 2021, now Pat. No. 11,521,321.

(51) Int. Cl.
*G06T 7/00* (2017.01)
*A61B 6/00* (2006.01)
(Continued)

(52) U.S. Cl.
CPC .............. *G06T 7/0012* (2013.01); *A61B 6/50* (2013.01); *A61B 6/5217* (2013.01);
(Continued)

(58) Field of Classification Search
CPC ......... G06T 7/0012; G06T 7/11; G06T 5/002; G06T 2207/10081; G06T 2207/20021;
(Continued)

(56) References Cited

U.S. PATENT DOCUMENTS

2020/0085382 A1\* 3/2020 Taerum ................. G06T 7/0016
2021/0042564 A1\* 2/2021 Xiao .................... A61B 5/7267
(Continued)

FOREIGN PATENT DOCUMENTS

CN 113539497 10/2021
WO 2017192965 A2 11/2017

OTHER PUBLICATIONS

Visvam S Nair, et al, Accuracy of Models to Identify Lung Nodule Cancer Risk in the National Lung Screening Trial, American Journal of Respiratory and Critical Care Medicine, 197(9), pp. 1220-1223, Oct. 24, 2017 NewYork, United States of America.

*Primary Examiner* — Samah A Beg
*Assistant Examiner* — Winta Gebreslassie

(57) ABSTRACT

Disclosed is a system and a method for determining a brock score. A CT scan image may be resampled into a plurality of slices using a bilinear interpolation. A nodule may be detected on one or more of the plurality of slices. A region of interest associated with the nodule may be identified using an image processing technique. Further, a nodule segmentation may be performed to remove an area surrounding the region of interest. Subsequently, a plurality of characteristics associated with the nodule may be identified automatically using a deep learning model. Finally, a brock score for the patient may be determined based on the plurality of characteristics and demographic data of the patient.

13 Claims, 4 Drawing Sheets

(51) Int. Cl.
*G06T 7/11* (2017.01)
*G06V 10/25* (2022.01)
*G06T 5/00* (2006.01)
*G16H 30/20* (2018.01)

(52) U.S. Cl.
CPC .......... *A61B 6/5258* (2013.01); *A61B 6/5294* (2013.01); *G06T 5/002* (2013.01); *G06T 7/11* (2017.01); *G06V 10/25* (2022.01); *G16H 30/20* (2018.01); *G06T 2207/10081* (2013.01); *G06T 2207/20021* (2013.01); *G06T 2207/20081* (2013.01); *G06T 2207/30064* (2013.01); *G06T 2207/30096* (2013.01)

(58) Field of Classification Search
CPC . G06T 2207/20081; G06T 2207/30064; G06T 2207/30096; G06T 2207/10072; G06T 2207/30061; G06T 2207/20084; G06T 11/001; G16H 30/20; G06V 10/25; A61B 6/50; A61B 6/5217; A61B 6/5258; A61B 6/5294
See application file for complete search history.

(56) References Cited

U.S. PATENT DOCUMENTS

2021/0285950 A1\* 9/2021 Kearney .................. G06N 7/01
2022/0148727 A1 5/2022 Arteta et al.

\* cited by examiner

AUTOMATICALLY DETERMINING A BROCK SCORE

RELATED APPLICATIONS

This application is a continuation-in-part of prior application U.S. Ser. No. 17/457,465, filed Dec. 3, 2021, which claims the benefit of Indian Patent application No. 202121045730, filed Oct. 7, 2021.

TECHNICAL FIELD

The present subject matter described herein, in general, relates to a system and a method for determining a brock score. More particularly, to monitoring a brock score using deep learning.

BACKGROUND

Typically, medical imaging techniques such as Computed Tomography (CT) scans and E-radiations (X-ray) scans are widely used by a health practitioner to detect lung cancers. It must be noted that an early detection of cancerous nodule is really important. Generally, a patient takes CT scans when he/she is suspected to have nodules in the chest. A health practitioner analyses the CT scans and manually identifies the nodules. Also, the health practitioners manually detect characteristics such as size and a location of the nodules. However, the manual detection and analysis is a time consuming and a cumbersome task. At times, the health practitioner may misjudge the nodules. Also, it may happen that the nodules, which are small in size go unnoticed. Therefore, there is a need for a method and system that accurately and automatically detects the presence of nodules.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for determining a brock score. This summary is not intended to identify essential features of the claimed subject matter nor is it intended for use in determining or limiting the scope of the claimed subject matter.

In one implementation, a method for determining a brock score for a patient is disclosed. Initially, a Computed Tomography (CT) scan image related to a chest region of the patient may be received. The CT scan image may be resampled into a plurality of slices using a bilinear interpolation. Further, a nodule on one or more of the plurality of slices may be detected based on an analysis of the plurality of slices using a first deep learning model. In an aspect, the first deep learning model may be trained using historical CT scans and historical nodules associated with a set of patients. The first deep learning model may detect patterns related to the historical nodules in the historical CT scans and process the one or more slices. Furthermore, a region of interest associated with the nodule may be identified based on an analysis of the nodule using an image processing technique. Subsequently, a nodule segmentation may be performed to remove an area surrounding the region of interest. The nodule segmentation may be performed using the first deep learning model. Further, a plurality of characteristics associated with the region of interest may be automatically determined using a second deep learning model. The second deep learning model may be trained using historical characteristics including a historical size of nodules, historical location of nodules, a historical spiculation of nodules, and a historical texture of nodules associated with the set of patients. The plurality of characteristics comprises a location of the nodule, a texture of the nodule, a size of the nodule, a spiculation of the nodule, and number of nodules present in the CT scan image. Finally, a brock score for the patient may be determined automatically in real-time based on the plurality of characteristics and demographic data of the patient. In one aspect, the aforementioned method for determining the brock score may be performed by a processor using programmed instructions stored in a memory.

In another implementation, a non-transitory computer readable medium embodying a program executable in a computing device for determining a brock score for a patient is disclosed. The program may comprise a program code for receiving a Computed Tomography (CT) scan image related to a chest region of the patient. Further, the program may comprise a program code for resampling the CT scan image into a plurality of slices using a bilinear interpolation. Furthermore, the program may comprise the program code for detecting a nodule on one or more of the plurality of slices based on an analysis of the plurality of slices using a first deep learning model. In an aspect, the first deep learning model may be trained using historical CT scans and historical nodules associated with a set of patients. The first deep learning model may detect patterns related to the historical nodules in the historical CT scans and process the one or more slices. The program may comprise a program code for identifying a region of interest associated with the nodule based on an analysis of the nodule using an image processing technique. Subsequently, the program may comprise the program code for performing a nodule segmentation to remove an area surrounding the region of interest. In an aspect, the nodule segmentation may be performed using the first deep learning model. Further, the program may comprise a program code for automatically determining a plurality of characteristics associated with the region of interest using a second deep learning model. The second deep learning model may be trained using historical characteristics including a historical size of nodules, historical location of nodules, a historical spiculation of nodules, and a historical texture of nodules associated with the set of patients. The plurality of characteristics may comprise a location of the nodule, a texture of the nodule, a size of the nodule, a spiculation of the nodule, and number of nodules present in the CT scan image. Finally, the program may comprise a program code for determining a brock score for the patient automatically in real-time based on the plurality of characteristics and demographic data of the patient.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for determining a brock score disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

Figure 1:
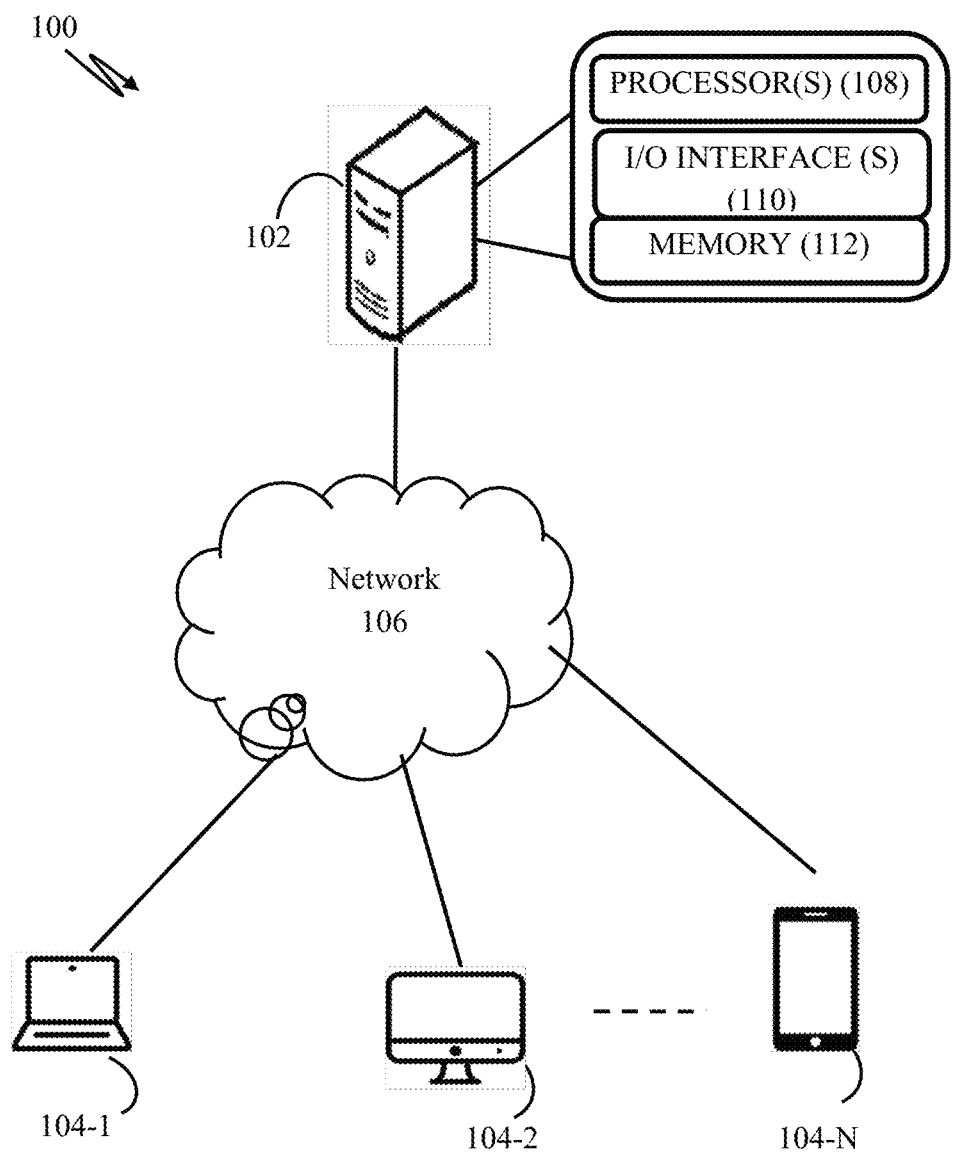
FIG. 1 illustrates a network implementation of a system for determining a brock score, in accordance with an embodiment of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving," "resampling," "detecting," "identifying," "performing," "determining," and other forms thereof, are intended to be open ended in that an item or items following any one of these words is not meant to be an exhaustive listing of such item(s) or meant to be limited to only the listed item(s). It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for determining a brock score. Typically, a doctor has to manually identify nodules in the CT scan image. Once the nodule is identified, the doctor manually performs analysis of the nodule to determine if the nodule is cancerous or not. This is a cumbersome and a time-consuming task. More importantly, the present invention discloses an efficient, and an automatic process for determining a brock score. The present invention determines the brock score in a real-time based on an analysis of a CT scan image related to a chest region of a patient. Further, the present invention generates a report comprising the brock score and other relevant information of the patient. Furthermore, the present invention provides remote assessment of the CT scan image. This helps to provide consultation to the patient remotely. Initially, the CT scan image of the patient may be received. Further, a nodule in the CT scan image may be detected. Subsequently, a region of interest associated with the nodule may be determined. Further, the brock score may be determined automatically based on identifying a plurality of characteristics associated with the region of interest. In one aspect, the one or more characteristics may be identified using deep learning model. In one embodiment, the present invention is configured to compute the brock score automatically using the deep learning model. While aspects of described system and method for determining a brock score may be implemented in any number of different computing systems, environments, and/or configurations, the embodiments are described in the context of the following exemplary system.

Referring now to FIG. 1, a network implementation 100 of a system 102 for determining a brock score is disclosed. It may be noted that one or more users may access the system 102 through one or more user devices 104-1, 104-2 . . . 104-N, collectively referred to as user devices 104, hereinafter, or applications residing on the user devices 104. In one aspect, the one or more users may comprise a health practitioner, a doctor, a lab assistant, a radiologist and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for determining a brock score. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for determining a brock score. The system 102 may monitor a Computed Tomography (CT) scan image in real-time. The CT scan image may be monitored using deep learning and image processing technique to determine the brock score of a patient. In order to determine the brock score, initially, the system 102 may receive the CT scan image related to a chest region of the patient. The CT scan image may be captured using a scanning device i.e. a medical scanner. The CT scan image may be a three-dimensional image. The CT scan image may be received from the user via the user device 104. The user may be one of a health practitioner, a doctor, a lab assistant, a radiologist and the like.

In one aspect, the CT scan image may be a Non-contrast CT series with axial cuts and soft reconstruction kernel which covers an entire Lung. The CT scan image may be one non-contrast CT series with consistently spaced axial slices. The CT scan image may comprise minimum of 40 axial slices in the series. The CT scan image may be available in a Digital Imaging and Communications in Medicine (DICOM) format. In one example, a maximum thickness of the CT scan image may be 6 mm.

In one embodiment, the system 102 may validate if the CT scan image is related to the chest region or not. The system 102 may use a machine learning model to validate the CT scan image. The machine learning model may be trained continuously in real-time using training data comprising historical chest region CT scan images associated with a set of patients. In an aspect, if the CT scan image is validated as the chest region CT scan, then the system 102 may proceed to analyze the CT scan image to determine the brock score. In another aspect, if the CT scan image is not related to the chest region or if there is no plain axial series, then the CT scan image may not be processed further. The system 102 may transmit a response to the user indicating that the uploaded series or the CT scan image is not valid and recommend rescanning.

In one embodiment, the system 102 may comprise a trained data model. The trained data model may be trained using historical data related to previous CT scans of the patient, one or more CT scans associated with a set of patients and the like. In one example, the trained data may comprise dataset containing 120,000 Chest CTs used for training and internally validating algorithms. The dataset may be referred to as 'development dataset'. The development dataset may be divided into training dataset and internal validation dataset using a 4:1 split. The resultant validation dataset (20% of the entire data) may be used to estimate the performance of the trained data model and for hyper-parameter tuning. In an aspect, the hyperparameter tuning may correspond to finding the optimal hyperparameters for any given machine learning algorithm.

In one aspect, the dataset in the trained data model may be large that results into multiple advantages. The dataset may comprise number of scans for all target abnormalities, allowing the development of accurate algorithm. An adequate number of control scans with various non-target abnormalities and normal variations may be likely to be present in the dataset. It may reduce the chances that these occurrences will negatively impact performance when the algorithm is deployed in the real world on previously unseen data. The selection of a large number of sources for the training data, rather than a large amount of data from a single site, may be advantageous because it allows the algorithms to be trained on the CT scan images from a wide variety of device manufacturers and CT protocols, without manually specifying the model name and specifications of the device.

In one embodiment, the system 102 may automate the checking of the DICOM for age, body part, contrast/non-contrast, slice thickness, view, and kernel. The system 102 may use a separate module called a series classifier which is described in detail in the preprocessing section. Further, the system 102 may check presence of a corresponding radiology report i.e., a ground truth, by matching the patient IDs. If no report is found, the CT scan image may be excluded. Subsequently, the system 102 may automate the checking of radiology report for the age. The system 102 may identify a number of cases which are labelled as CHEST in the DICOM attribute but are not actually Chest CT scan images, such CT scan images may be identified using the trained series classifier and not used in training or testing (these can be considered outliers).

In one embodiment, only requirement for training the system 102 may be the presence of the DICOM data and a text report. Once these requirements are met, the concept of missing values or missing data may not apply as it does for other machine learning algorithms. There may be no other exclusions from the training dataset.

In one aspect, an automated natural language processing based labeling approach may be chosen as the primary method for generating the ground truth. Additionally, a number of pixel-level hand annotations may be used to either further improve accuracy or to provide input to a segmentation algorithm. It may be noted that an intended use of the system 102 is to aid in the interpretation of the Chest CT images, therefore the labeling method that largely depends on the radiology reports, which are the ground truth for these images, is appropriate.

Each Chest CT scan image in the training dataset may have a single corresponding the ground truth, generated during the normal course of clinical care. The ground truth includes at least the radiology report and a biopsy report where available. The ground truth is used for training the algorithm.

The Natural Language Processing (NLP) algorithms may be developed based on rules/dictionaries, trained with machine learning techniques, or a combination of the two approaches. Rule based NLP algorithm may use a list of manually created rules to parse the unorganized content and structure it. Machine Learning (ML) based NLP algorithm, on the other hand, may automatically generate the rules when trained on a large annotated dataset. The rule-based NLP algorithm may be chosen over a machine-learning based NLP algorithm for the purpose of labeling radiology reports.

The rule-based NLP algorithm may have few advantages comprising clinical knowledge can be manually incorporated into the rule-based NLP algorithm. In order to capture this knowledge in the ML based algorithm, a huge amount of annotation may be required. Further, rules may be readily added or modified to accommodate a new set of target findings in the rule-based NLP algorithm.

Once the CT scan image is received, the system 102 may apply a gaussian smoothing method on the CT scan image. The gaussian smoothing method may be configured to counteract noise. In other words, the gaussian smoothing method may reduce image noise and enhance a structure of the CT scan image. In one aspect, the gaussian smoothing may be applied in a z dimension (i.e., longitudinal axis). In one example, a gaussian kernel used for the gaussian smoothing may have a sigma of 1 mm in the z dimension, and 0 in other dimensions. The gaussian smoothing may have a negligible effect on the CT scan image with thickness greater than 2 mm as the gaussian kernel decays by 95% at 2*sigma (=2 mm). In one aspect, the gaussian smoothing may help to remove noise from the CT scan image.

Subsequently, the system 102 may resample the CT scan image into a plurality of slices. The CT scan image may be resampled using a bilinear interpolation. The bilinear interpolation may use the distance weighted average of the four nearest pixel values to estimate a new pixel value. In one aspect, the system 102 may resample the CT scan image so that its slice thickness is around 2.5 mm. The system 102 may obtain a resampling factor by dividing 2.5 by the series' slice thickness and rounding the result to an integer. The rounding may be used to ensure that there are no resampling artifacts.

Further, the system 102 may detect a nodule one or more of the plurality of slices. The nodule may be detected based on an analysis of the plurality of slices using a first deep learning model. The first deep learning model may be trained using historical CT scans and historical nodules associated with the set of patients. The first deep learning model may detect patterns in the historical CT scans and process the one or more slices. The patterns may be related to the detection of the historical nodule on the historical CT scans. The processing of the one or more slices may comprise analysis of the slices using the patterns to detect the nodule on the one or more slices. In one aspect, the first deep learning model may be configured to determine whether the nodule on the one or more slices matches with at least one of the historical nodules. The system 102 may receive an output from the first deep learning model indicating whether the nodule matches with the historical nodules. In one embodiment, the first deep learning model may analyze the plurality of slices using training data i.e., the historical CT scans and the historical nodule in order to detect the nodule. In one aspect, the nodule may be present in multiple slices. Once the nodule matches with the one of the historical nodules, the system 102 may detect it as confirmed nodule.

In one aspect, the system 102 may comprise a Se-ResNeXt50 model to detect the nodule. The Se-ResNeXt50 may be a modified version of ResneXt50 a popular neural network architecture which has 50 layers with increased inter layer connectivity. The model may have 50 convolutional layers, modified to take in regional information and softmax based confidences. Further, the system 102 may comprise U-Net and FPN. The U-Net and FPN may be a popular segmentation architecture for biomedical segmentation. The U-Net and FPN may have five downsampling and five upsampling blocks of convolutional layers with skip connections.

Figure 2:
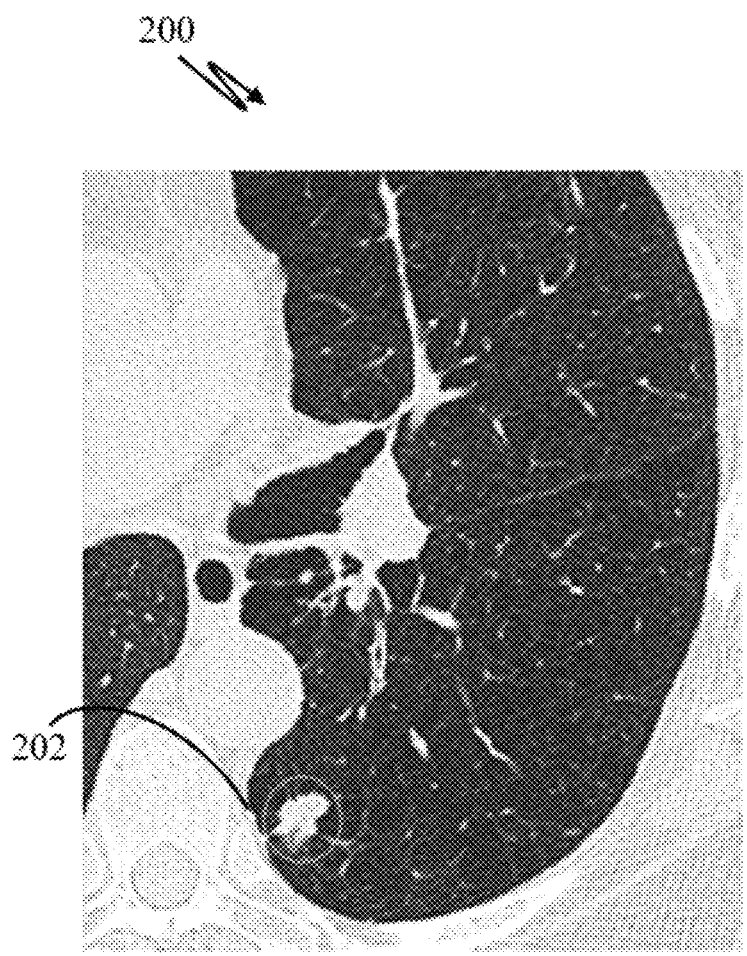
FIG. 2 shows a block diagram for determination of a brock score, in accordance with an embodiment of the present subject matter.

Referring now to FIG. 2, the structure of the nodule is shown, in accordance with an embodiment of the present subject matter. In one embodiment, the CT scan image 200 of the patient may be received. Further, the system 102 may detect the nodule 202. In one example, the nodule may be a rounded or irregular opacity, well or poorly defined, measuring up to 3 cm in the diameter.

In one embodiment, the system 102 may use the neural network architecture for slice-wise inference. It is an FPN with SE-ResNext-50 backbone with classification and segmentation heads. Weights of the Convolutional Neural Network (CNN) may be used to process each slice may be 'tied' and thus share the same weights.

Slice level classification output may be pooled into scan level output using following operation as shown in equation 1.

$$P\text{scan} = \Sigma i = 0 \text{ to } \#slices w_i * P\text{slice}_i \qquad \text{Equation 1}$$

Wherein $w_i$ may be softmax weights computed as shown in equation 2.

$$w_i = \exp(P\text{slice}_i) / \Sigma i = 0 \text{ to } \#slices \exp(P\text{slice}_i) \qquad \text{Equation 2}$$

In one aspect, essentially the system 102 may comprise a softer version of max pooling used in CNNs. The operation may be referred as 'softmaxpooling'. The model architecture may comprise three outputs: scan-level probability, list of slice-level probabilities of presence of nodules and a 3D segmentation mask of nodules.

Referring again to FIG. 1, once the nodule is detected, the system 102 may identify a region of interest associated with the nodule. The region of interest may be identified based on an analysis of the nodule. The system 102 may use an image processing technique to identify the region of interest. The system 102 may analyze the plurality of slices using the image processing technique and mark the region of interest. In one aspect, the region of interest may indicate an abnormality on each slice.

In one embodiment, a small part of the CT scan image may be annotated at a pixel level which serve as the secondary labels to the training algorithms. It may include the region of interest annotation (lung, diaphragm, mediastinum and ribs) as well as abnormality pixel-wise annotation which are then used to derive the Region of Interest (ROI) level annotations. In one example, 5% of the Chest CT scan images may be duplicated, as a test for competency of the annotators. If there was less than 75% concordance the CT scan image will be re-annotated. These discrepancies may be tracked as a way to continually test the accuracy of the annotations and the competency of the annotators.

Once the region of interest is identified, the system 102 may perform a nodule segmentation to remove an area surrounding the region of interest. The nodule segmentation may be performed using the first deep learning model. The nodule segmentation may correspond to masking of the region of interest. In an aspect, once the nodule is detected and the region of interest is identified, the system 102 may mask the region of interest to remove the area. The area may be black or air areas and fatty tissues around the region of interest. Removing these areas may help to focus on the region of interest. The masking may help to improve performance of a detection algorithm.

Further, the system 102 may automatically determine plurality of characteristics associated with the region of interest. The plurality of characteristics may be identified using a second deep learning model. In an aspect, the second deep learning model may be trained using historical characteristics identified for the historical nodules associated with the set of patients. The historical characteristics may include a historical size of nodules, historical location of nodules, a historical spiculation of nodules, and a historical texture of nodules associated with the set of patients. In the aspect, historical data associated with the set of patients may be used to train the second deep learning model. The second deep learning model may analyze the region of interest using the historical data in order to determine the plurality of characteristics of the region of interest. The system 102 may further receive an output related to the plurality of characteristics from the second deep learning model. In one embodiment, the system 102 may receive user's feedback in order train the second deep learning model. The continuous training of the second deep learning model may help for an accurate determination of the plurality of characteristics. In an aspect, the plurality of characteristics may be determined in real-time.

Further, the plurality of characteristics may comprise a location of the nodule, a texture of the nodule, a size of the nodule, a spiculation of the nodule, and number of nodules present in the chest CT scan image. In one embodiment, the location of the nodule may be one of an upper right area of the chest region, an upper left area of the chest region, a lower right area of the chest region and a lower left area of the chest region. The texture of the nodule may be one of a solid nodule, a partially solid nodule and a non-solid nodule. The size of the nodule may correspond to a diameter of the nodule. The spiculation of the nodule may indicate a border of the nodule. Further, the number of nodules present in the CT scan image may be computed by the system 102. In one embodiment, the system 102 may use a Convolution Neural Network (CNN) module to determine the plurality of characteristics. In one example, the diameter of the nodule may be further used to determine a total volume of the nodule and an area covered by the nodule.

Upon determining the plurality of characteristics, the system 102 may determine a brock score for the patient. The brock score may be determined automatically in real-time. The brock score may be determined based on the plurality of characteristics and demographic data of the patient. The demographic data may a patient name, a patient age, a patient gender, and patient's family medical history. In an aspect, the system 102 may receive the demographic data from the patient, the patient's guardian and the like. In another aspect, the system 102 may capture the patient's name, the patient's age and the patient's gender by analyzing the CT scan image using a natural language processing technique. The patient's family medical history may correspond to the history of the patient's family regarding a lung cancer. In one example, the brock score may be valid for: Age >18 yrs, Nodule Size 1 mm to 30 mm, Nodule Count <100.

In one embodiment, the system 102 may assign a weightage to each of the plurality of characteristics. Further, the weightage of each characteristic and the demographic data of the patient may be used to determine the brock score in real-time.

In one aspect, the brock score may indicate a probability of a lung cancer related to the nodule detected in the chest CT scan image of the patient. Subsequently, the system 102 may compare the brock score with a brock threshold. Based on the comparison, the system 102 may recommend a next course of action for the patient. The next course of action may comprise a follow-up with the health practitioner. In one embodiment, if the brock score is greater than or equal to the brock threshold, it may indicate that the nodule detected in the CT scan image is cancerous. In another embodiment, if the brock score is less than brock threshold, it may indicate that the nodule is non-cancerous. In one example, the health practitioner may use the brock score to determine appropriate follow-up time and management of the nodules detected on the CT scan image. In one embodiment, the system 102 may detect an emphysema in the CT scan image. The emphysema may correspond to a destruction of lung tissues. The emphysema may be detected using the first deep learning model. The first deep learning model may be trained continuously trained using previous emphysema data associated with the set of patients. The detection of the emphysema may indicate that there is a low chance of cancerous. The emphysema may be used to determine the brock score. In one aspect, the weightage may be assigned to emphysema. Further, the system 102 may use the emphysema, the plurality of characteristics and the demographic data to determine the brock score.

Further, the system 102 may generate a report of the patient. The report may be generated in real-time. The report may comprise the detected nodule, the detected emphysema, the brock score and the next course of action. In one aspect, the health practitioner may analyze the report and provide consultation to the patient remotely. In one aspect, the system 102 may notify the patient regarding the follow-up with the health practitioner. The follow-up may be notified based on the brock score. In one aspect, the system 102 may allow the health practitioner to provide feedback on the report. The health practitioner may be allowed to annotate the nodule detected in the CT scan image.

In one embodiment, the system 102 may comprise a false positive detection module. The false detection module may determine false positive nodules on each slice. The false positive nodules may be determined using a 3-dimensional CNN model. The false positive nodules may be determined by comparing the nodules with the historical nodules. In one embodiment, the system 102 may use the location and the diameter of the nodule to determine the false positive nodules.

Figure 3:
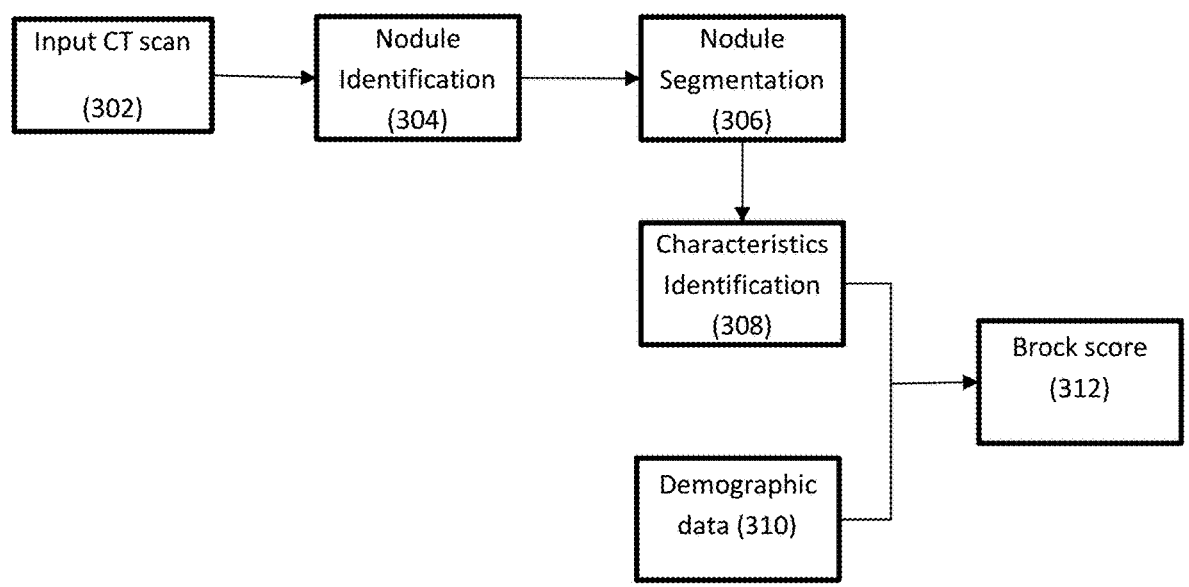
FIG. 3 shows a structure of a nodule, in accordance with an embodiment of the present subject matter.

Referring now to FIG. 3, a block diagram for determining a brock score is shown, in accordance with an embodiment of the present subject matter. In one embodiment, at block 302, a CT scan image related to a chest region of a patient may be received. Further, At block 304, the CT scan image may be analyzed using deep learning to detect a nodule. The nodule may be detected on one or more slices from a plurality of slices of the CT scan image. Further, at block 306, a nodule segmentation may be performed to remove an area surrounding the nodule. The nodule segmentation may help to focus on the nodule. Upon nodule segmentation, a region of interest related to the nodule may be identified. Subsequently, at block 308, a plurality of characteristics related to the nodule may be identified automatically using the deep learning. The plurality of characteristics may include a size, a location, a spiculation, a texture and number of nodules present in the CT scan image. The plurality of characteristics and demographic data at block 310 may be used to determine the brock score at block 312. The brock score may be used to predict a lung cancer risk for the patient.

Figure 4:
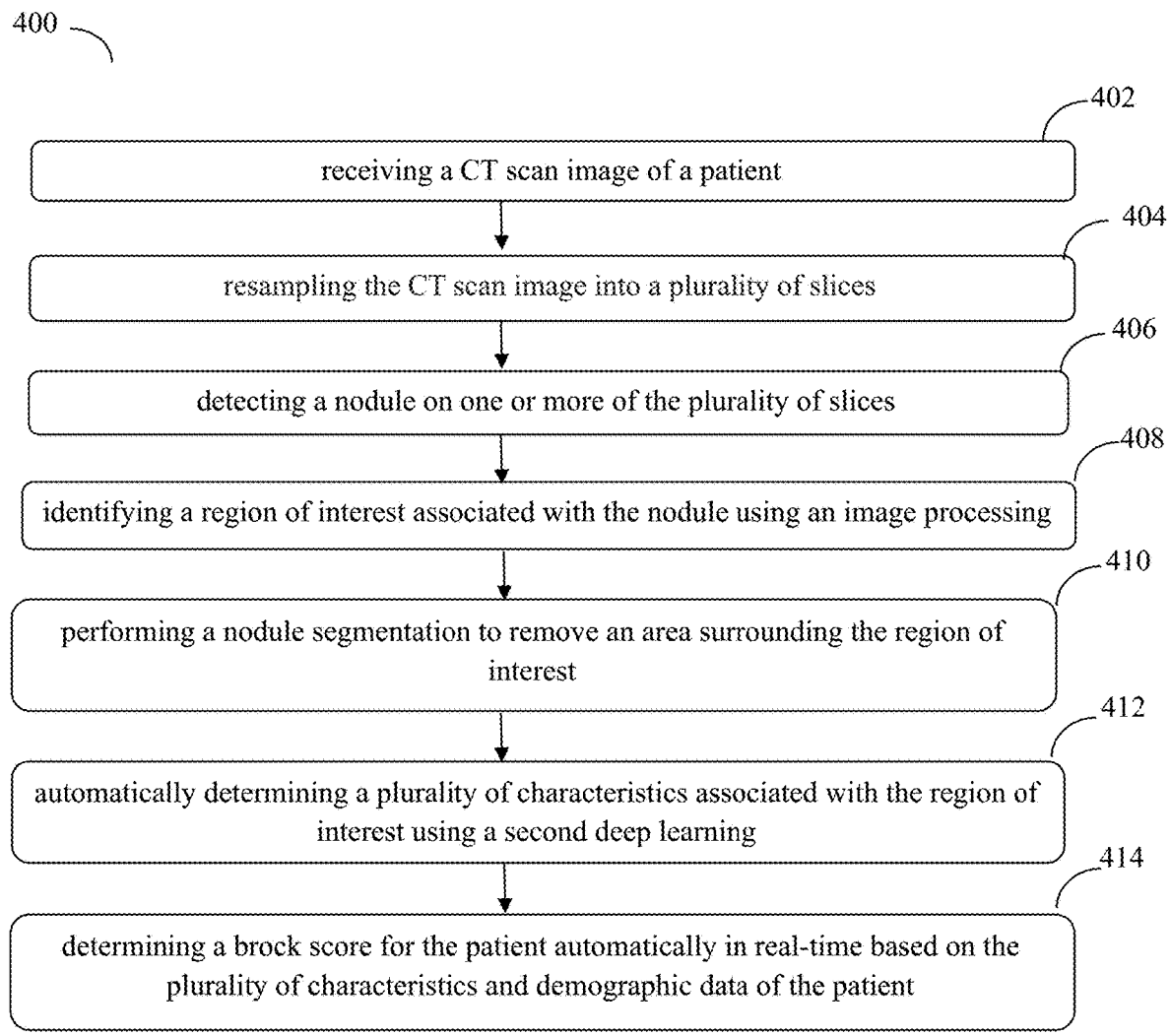
FIG. 4 illustrates a method for determining a brock score, in accordance with an embodiment of the present subject matter.

Referring now to FIG. 4, a method 400 for determining a brock score for a patient is shown, in accordance with an embodiment of the present subject matter. The method 400 may be described in the general context of computer executable instructions. Generally, computer executable instructions can include routines, programs, objects, components, data structures, procedures, modules, functions, etc., that perform particular functions or implement particular abstract data types.

The order in which the method 400 is described is not intended to be construed as a limitation, and any number of the described method blocks can be combined in any order to implement the method 400 or alternate methods for determining the brock score. Additionally, individual blocks may be deleted from the method 400 without departing from the spirit and scope of the subject matter described herein. Furthermore, the method 400 for determining the brock score can be implemented in any suitable hardware, software, firmware, or combination thereof. However, for ease of explanation, in the embodiments described below, the method 400 may be considered to be implemented in the above-described system 102.

At block 402, a Computed Tomography (CT) scan image related to a chest region of the patient may be received.

At block 404, the CT scan image may be resampled into a plurality of slices using a bilinear interpolation.

At block 406, a nodule may be detected on one or more of the plurality of slices based on an analysis of the plurality of slices using a first deep learning model. In an aspect, the first deep learning model may be trained using historical CT scans and historical nodules associated with a set of patients. The first deep learning model may detect patterns related to the historical nodules in the historical CT scans and process the one or more slices.

At block 408, a region of interest associated with the nodule may be identified based on an analysis of the nodule using an image processing technique.

At block 410, a nodule segmentation may be performed to remove an area surrounding the region of interest. In an aspect, the nodule segmentation may be performed using the first deep learning model.

At block 412, a plurality of characteristics associated with the region of interest may be automatically determined using a second deep learning model. In an aspect, the second deep learning model may be trained using historical characteristics including a historical size of nodules, historical location of nodules, a historical spiculation of nodules, and a historical texture of nodules associated with the set of patients. The plurality of characteristics may comprise a location of the nodule, a texture of the nodule, a size of the nodule, a spiculation of the nodule, and number of nodules present in the CT scan image.

At block 414, a brock score for the patient may be determined automatically in real-time based on the plurality of characteristics and demographic data of the patient.

Exemplary embodiments discussed above may provide certain advantages. Though not required to practice aspects of the disclosure, these advantages may include those provided by the following features.

Some embodiments of the system and the method enable identifying characteristics of a nodule automatically using deep learning.

Some embodiments of the system and the method enable detecting a nodule and an emphysema using a Convolution Neural Network (CNN) model.

Some embodiments of the system and the method enable identifying false positive nodules using a 3-directional CNN model.

Some embodiments of the system and the method enable computing a brock score using a plurality of characteristics and deep learning technique, which further helps to predict a lung cancer risk for a patient.

Some embodiments of the system and the method enable an improvement in a traditional method of identifying the brock score.

Some embodiments of the system and the method enable an efficient and an accurate process using the large dataset.

Although implementations for methods and system for determining a brock score have been described in language specific to structural features and/or methods, it is to be understood that the appended claims are not necessarily limited to the specific features or methods described. Rather, the specific features and methods are disclosed as examples of implementations for determining the brock score.

The invention claimed is:

1. A method to determine a brock score for a patient:
receiving, by a processor, a Computed Tomography (CT) scan image related to a chest region of the patient;
resampling, by the processor, the CT scan image into a plurality of slices by applying a bilinear interpolation on a distance weighted average of surrounded pixel values;
detecting, by the processor, a nodule on one or more of the plurality of slices based on an analysis of the plurality of slices using a first deep learning, wherein the first deep learning is trained using historical CT scans and historical modules associated with a set of patients, and wherein the first deep learning model is configured to detect patterns related to the historical nodules in the historical CT scans and process the one or more slices;
identifying, by the processor, a region of interest associated with the nodule based on an analysis of the nodule using an image processing technique;
masking, by the processor, the region of interest to perform a nodule segmentation by removing an area, including at least one of black areas and fatty tissues, surrounding the region of interest, wherein the nodule segmentation is performed using the first deep learning model;
automatically determining, by the processor, a plurality of characteristics associated with the region of interest using a second deep learning model, wherein the second deep learning model is trained using historical characteristics including a historical size of nodules, historical location of nodules, a historical spiculation of nodules, and a historical texture of nodules associated with the set of patients, wherein the plurality of characteristics comprises a location of the nodule, a texture of the nodule, a size of the nodule, a speculation of the nodule, and number of nodules present in the CT scan image; and determining, by the processor, a brock score for the patient automatically in real-time based on the plurality of characteristics and demographics data of the patient.

2. The method as claimed in claim 1, comprises applying a gaussian smoothing method on the CT scan image to counteract noise.

3. The method as claimed in claim 1, wherein the demographic data of the patient comprises a patient name, patient age, a patient gender, and patient's medical family history.

4. The method as claimed in claim 1, comprises recommending a next course of action for the patient based on comparing the brock score with a brock threshold, and wherein the next course of action comprise a follow-up with a health practitioner.

5. The method as claimed in claim 1, wherein the brock score indicates a probability of a lung cancer related to the nodule detected in the chest CT scan image of the patient.

6. The method as claimed in claim 1, comprises detecting an emphysema in the region of interest of each slice of the chest CT scan image using the second deep learning, and wherein the emphysema is used to determine the brock score.

7. A system for determining a brock score, the system comprising:
a memory;
a processor coupled to the memory, wherein the processor is configured to execute instructions stored in the memory to:
receive a Computed Tomography (CT) scan image related to a chest region of the patient;
resample the CT scan image into a plurality of slices by applying a bilinear interpolation on a distance weighted average of surrounded pixel values;
detect a nodule on one or more of the plurality of slices based on an analysis of the plurality of slices using a first deep learning, wherein the first deep learning is trained using historical CT scans and historical modules associated with a set of patients, and wherein the first deep learning model is configured to detect patterns related to the historical nodules in the historical CT scans and process the one or more slices;
identify a region of interest associated with the nodule based on an analysis of the nodule using an image processing technique;
mask, the region of interest to perform a nodule segmentation by removing an area, including at least one of black areas and fatty tissues, surrounding the region of interest, wherein the nodule segmentation is performed using the first deep learning model;
automatically determine a plurality of characteristics associated with the region of interest using a second deep learning model, wherein the second deep learning model is trained using historical characteristics including a historical size of nodules, historical location of nodules, a historical speculation of nodules, and a historical texture of nodules associated with the set of patients, wherein the plurality of characteristics comprises a location of the nodule, a texture of the nodule, a size of the nodule, a specu-
lation of the nodule, and number of nodules present in the CT scan image; and
determine a brock score for the patient automatically in real-time based on the plurality of characteristics and demographics data of the patient.

8. The system as claimed in claim 7, comprises applying a gaussian smoothing method on the CT scan image to counteract noise.

9. The system as claimed in claim 7, wherein the demographic data of the patient comprises a patient name, patient age, a patient gender, and patient's medical family history.

10. The system as claimed in claim 7, comprises recommending a next course of action for the patient based on comparing the brock score with a brock threshold, and wherein the next course of action comprises a follow-up with a health practitioner.

11. The system as claimed in claim 7, wherein the brock score indicates a probability of a lung cancer related to the nodule detected in the chest CT scan image of the patient.

12. The system as claimed in claim 7, comprises detecting an emphysema in the region of interest of each slice of the chest CT scan image using the second deep learning, and wherein the emphysema is used to determine the brock score.

13. A non-transitory computer program product having embodied thereon a computer program for determining a brock, the computer program product storing instructions, the instructions comprising instructions for:
receiving a Computed Tomography (CT) scan image related to a chest region of the patient;
resampling the CT scan image into a plurality of slices by applying a bilinear interpolation on a distance weighted average of surrounded pixel values;
detecting a nodule on one or more of the plurality of slices based on an analysis of the plurality of slices using a first deep learning, wherein the first deep learning is trained using historical CT scans and historical modules associated with a set of patients, and wherein the first deep learning model is configured to detect patterns related to the historical nodules in the historical CT scans and process the one or more slices;
identifying a region of interest associated with the nodule based on an analysis of the nodule using an image processing technique;
masking the region of interest to perform a nodule segmentation by removing an area, including at least one of black areas and fatty tissues, surrounding the region of interest, wherein the nodule segmentation is performed using the first deep learning model;
automatically determining a plurality of characteristics associated with the region of interest using a second deep learning model, wherein the second deep learning model is trained using historical characteristics including a historical size of nodules, historical location of nodules, a historical speculation of nodules, and a historical texture of nodules associated with the set of patients, wherein the plurality of characteristics comprises a location of the nodule, a texture of the nodule, a size of the nodule, a speculation of the nodule, and number of nodules present in the CT scan image; and
determining a brock score for the patient automatically in real-time based on the plurality of characteristics and demographics data of the patient.

* * * * *